(12) United States Patent
Paschalides

(10) Patent No.: US 11,655,256 B1
(45) Date of Patent: May 23, 2023

(54) PROCESSES FOR MAKING A SOLID-STATE FORM OF RELUGOLIX

(71) Applicant: Johnson Matthey Public Limited Company, London (GB)

(72) Inventor: Nicholas Paschalides, Devens, MA (US)

(73) Assignee: Macfarlan Smith Limited, Edinburgh ( * ) Notice: Subject to any disclaimer, the term of this patent is extended or adjusted under 35 U.S.C. 154(b) by 0 days.

(21) Appl. No.: 17/520,642

(22) Filed: Nov. 6, 2021

Related U.S. Application Data

(60) Provisional application No. 63/198,711, filed on Nov. 6, 2020.

(51) Int. Cl.
*C07D 495/04* (2006.01)

(52) U.S. Cl.
CPC .................... *C07D 495/04* (2013.01)

(58) Field of Classification Search
CPC ..................................... C07D 495/04
See application file for complete search history.

(56) References Cited

U.S. PATENT DOCUMENTS 9,758,528 B2   9/2017   Fukuoka
10,464,945 B2  11/2019  Miwa

*Primary Examiner* — Rebecca L Anderson

(57) ABSTRACT

The present invention is directed to processes for making an anhydrous form of relugolix, designated herein as Form T of anhydrous relugolix. The processes of making Form T of anhydrous relugolix are from the following: (i) Form A of the DMF solvate of relugolix; (ii) Form B of anhydrous relugolix; or (iii) amorphous relugolix.

22 Claims, 17 Drawing Sheets

PROCESSES FOR MAKING A SOLID-STATE FORM OF RELUGOLIX

FIELD OF THE INVENTION

The invention relates to processes for making an anhydrous form of relugolix, designated herein as Form T of anhydrous relugolix.

BACKGROUND OF THE INVENTION

Relugolix, having the chemical designation, 1-[4-[1-[(2,6-difluorophenyl)-methyl]-5-[(dimethylamino)methyl]-3-(6-methoxypyridazin-3-yl)-2,4-dioxothieno-[2,3-d]pyrimidin-6-yl]phenyl]-3-methoxyurea, is an orally active nonpeptide gonadotropin-releasing hormone (GnRH)-receptor antagonist. Relugolix has the following structure:

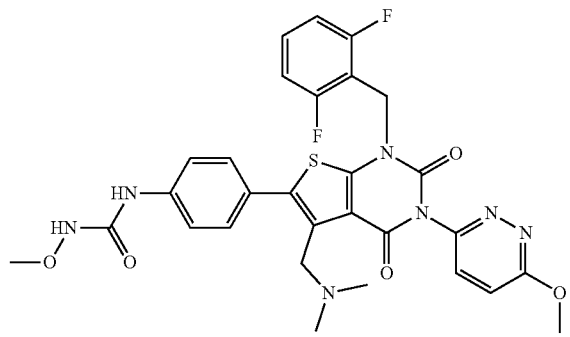

Relugolix has been approved in Japan as a treatment for symptoms associated with uterine fibroids. Studies are ongoing to evaluate the efficacy of relugolix as a treatment for endometriosis-associated pain and prostate cancer.

U.S. Pat. Nos. 10,464,945 and 9,758,528 disclose a crystalline form of a tetrahydrofuran solvate of relugolix, and another crystalline form that exhibits an x-ray powder diffraction pattern having 2-theta (2θ) peaks at approximately 7.384°, 8.932°, 9.933°, 12.076°, 16.607°, 17.328°, 22.202°, 22.761°, and 27.422° 2θ. U.S. Pat. Nos. 10,464,945 and 9,758,528 also disclose a method of producing a crystal of 1-{4-[1-(2,6-difluorobenzyl)-5-dimethylaminomethyl-3-(6-methoxypyridazin-3-yl)-2,4-dioxo-1,2,3,4-tetra hydrothieno[2,3-d]pyrimidin-6-yl]phenyl}-3-methoxyurea (relugolix) or a salt thereof, which comprises recrystallizing a crystal of a tetrahydrofuran solvate of 1-{4-[1-(2,6-difluorobenzyl)-5-dimethylaminomethyl-3-(6-methoxypyridazin-3-yl)-2,4-dioxo-1,2,3,4-tetrahydrothieno[2,3-d]pyrimidin-6-yl]phenyl}-3-methoxyurea or a salt thereof using an alkyl alcohol and one solvent selected from the group consisting of dimethylsulfoxide, dimethylformamide and dimethylacetamide.

SUMMARY OF THE DISCLOSURE

The present invention is directed to processes of making Form T of anhydrous relugolix from the following: (i) Form A of the DMF solvate of relugolix; (ii) Form B of anhydrous relugolix; or (iii) amorphous relugolix.

DETAILED DESCRIPTION OF THE DISCLOSURE

Figure 1:
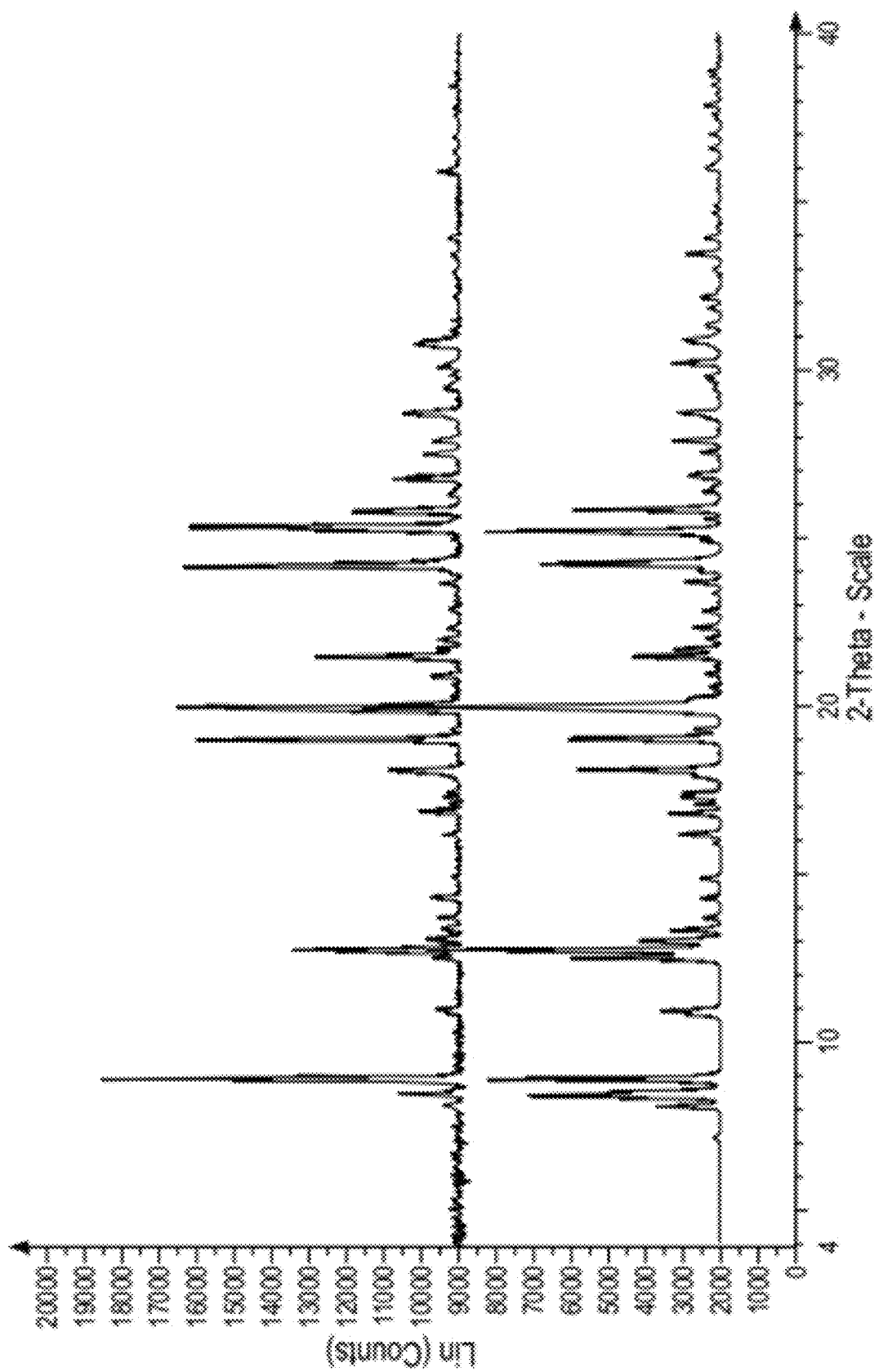
FIG. 1 provides an overlay of a calculated XRPD pattern from a single crystal of Form A of the DMF solvate of relugolix (bottom) and actual XRPD pattern of Form A of the DMF solvate of relugolix (top).

The present disclosure is directed to processes of making Form T of anhydrous relugolix from the following: (i) Form A of the DMF solvate of relugolix; (ii) Form B of anhydrous relugolix; or (iii) amorphous relugolix.

As used herein and unless otherwise specified, the term "solid-state form" includes crystalline or polymorphic forms, amorphous phase, and solvates.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

As used herein and unless otherwise specified, the terms "polymorph," "polymorphic form" or related term herein, refer to a crystal form of an API (active pharmaceutical ingredient) free base or salt thereof that can exist in two or more forms, as a result of different arrangements or conformations of the molecule, ions of the salt, or addition and arrangement of solvents within the crystalline lattice.

As used herein and unless otherwise specified, the terms "substantially" or "substantially free/pure" with respect to a polymorph or polymorphic form means that the form contains about less than 30 percent, about less than 20 percent, about less than 15 percent, about less than 10 percent, about less than 5 percent, or about less than 1 percent by weight of impurities. Impurities may, for example, include other polymorphic forms, water and solvents other than that in a solvated crystalline polymorphic form.

As used herein and unless otherwise specified, the abbreviation "DMF" refers to dimethylformamide; the abbreviation "TBME" refers to tert-butylmethyl ether; and the abbreviation "DCM" refers to dichloromethane.

Techniques for characterizing crystal and amorphous forms include but are not limited to differential scanning calorimetry (DSC), thermal gravimetric analysis (TGA), dynamic vapor sorption (DVS), X-ray powder diffractometry (XRPD), single crystal X-ray diffraction (SCXRD), proton nuclear magnetic resonance ($^1$H-NMR), Fourier transform infrared spectroscopy (FTIR Spectroscopy), and Optical Microscopy.

TGA data are collected using a TA Instruments TGA Q500. Samples (about 2-5 mg) are placed in a pin holed sealed hermetic alodined aluminum DSC pan, pre-tared with an aluminum pan and scanned from about 30 to about 300° C. at a rate of about 10° C./min using a nitrogen purge at about 60 mL/min.

X-ray powder diffraction patterns are obtained using a Bruker D8 Advance equipped with a Cu Kα radiation source (λ=1.54° A), a 9-position sample holder and a LYNXEYE super speed detector. Samples are placed on air sensitive silicon plate holders with zero-background with domes, for analysis. One skilled in the art would recognize that the °2θ values and the relative intensity values are generated by performing a peak search on the measured data and that the d-spacing values can be calculated by the instrument from the °2θ values using Bragg's equation. One skilled in the art would further recognize that the relative intensity for the measured peaks may vary as a result of sample preparation, orientation and instrument used, for example.

The X-ray intensity data for SCXRD are collected on a Bruker D8QUEST [1] CMOS area detector employing graphite-monochromated Mo-Kα radiation (λ=0.71073 Å) at a temperature of 100 K.

DVS samples are analyzed using a TA Instruments Q5000SA gravimetric water sorption analyzer. The relative humidity is adjusted between about 0-95% and the weight of the sample is continuously monitored and recorded with respect to the relative humidity and time.

DSC data are collected using a TA Instruments Q10 DSC. About 2-8 mg of sample are placed in sealed but covered hermetic alodined aluminum sample pan and scanned from about 30 to about 300° C. at a rate of about 10° C./min under a nitrogen purge of about 50 mL/min. Additionally, DSC runs are generated on a TA Instruments Q2000 equipped with an auto-sampler and RSC40. The instrument is programmed with about a 10° C./min ramp rate from about 25° C. to about 300° C. using Tzero hermetically sealed aluminum pans in T4P (or T4) mode.

$^1$H NMR samples are prepared by dissolving the compound in deuterated dimethylsulfoxide and deuterated chloroform with about 0.05% (v/v) tetramethylsilane (TMS). Spectra are collected at ambient temperature on a Bruker Avance 600 MHz NMR equipped with TopSpin software. The number of scans is 16 for $^1$H-NMR at 298 K.

Form A of the DMF solvate of relugolix is prepared by:
a) mixing a solution of relugolix in DMF with an anti-solvent; and
b) stirring the mixture of step a) to yield Form A of the DMF solvate of relugolix as a precipitate.

In one embodiment, the ratio of relugolix to DMF in the solution of relugolix in DMF is about 1:5 weight ($g_{relugolix}$) to volume ($mL_{DMF}$). In a particular embodiment, the anti-solvent is TBME. In another embodiment the anti-solvent is toluene. It will be apparent to one of ordinary skill in the art that other anti-solvents, such as, for example but without being limited to, heptane, xylene, or cumene, can be used depending on their anti-solvent properties. In one embodiment, about 10-13 volumes of anti-solvent is mixed with the solution of relugolix in DMF (weight ($g_{relugolix}$) to volume ($mL_{anti-solvent}$)). In one embodiment, the anti-solvent is added to the solution of relugolix in DMF. In a particular embodiment, the precipitation occurs at ambient temperature. Another embodiment further comprises reducing the temperature of the mixture of the solution of relugolix in DMF and anti-solvent to the nucleation temperature for about 30 minutes to 1 hour to produce a precipitate. The nucleation temperature is readily determined by one of ordinary skill in the art. The temperature is slowly lowered from the nucleation temperature about 2-5° C. per minute to about 5° C. Another embodiment is wherein larger particles of relugolix are produced. In one embodiment, the stirring occurs for about 15-18 hours. In other embodiments, the stirring occurs for a shorter period of time. Another embodiment further comprises isolating the precipitate. Another embodiment further comprises using additional anti-solvent to facilitate the isolating of the precipitate. Another embodiment further comprises using additional anti-solvent to wash the precipitate. In one embodiment, the isolating is effected by vacuum filtration. One embodiment further comprises drying the precipitate. In one embodiment, the drying is under vacuum at about 45° C. In one embodiment, the drying occurs for at least about 8 hours to overnight (about 16-24 h). Another embodiment further comprises preparing the solution of relugolix in DMF by dissolving relugolix in DMF. In one embodiment, the relugolix is dissolved in DMF at ambient temperature. In another embodiment, heat is applied to facilitate the dissolution. Another embodiment further comprises preparing the solution of relugolix in DMF by combining relugolix and DMF, wherein the relugolix is formed by a chemical reaction in solution, for example, by deprotection. It will be apparent to one of ordinary skill in the art that any relugolix may be used, regardless of its solid-state form, in the solution of relugolix in DMF. Depending on the purity of the relugolix, it may be necessary or desirable to remove any or all unwanted salts from the relugolix by water extractions or to remove any or all other impurities before preparing the solution of relugolix in DMF.

Form B of anhydrous relugolix is prepared by
a) forming a solution of relugolix in DCM wherein the relugolix is in about 20 volumes of DCM (weight ($g_{relugolix}$):volume($mL_{DCM}$)); and b) evaporating the DCM to yield Form B of anhydrous relugolix.

One embodiment further comprises preparing the solution of relugolix in DCM by dissolving relugolix in DCM. Another embodiment further comprises preparing the solution of relugolix in DCM by combining relugolix and DCM, wherein the relugolix is formed by a chemical reaction in solution, for example, by deprotection. In another embodiment the evaporating the DCM is carried out with a rotary evaporator at about 35° C. and under a high vacuum pump for at least about 3 hours. It will be apparent to one of ordinary skill in the art that any relugolix may be used, regardless of its solid-state form, in the solution of relugolix in DCM. Depending on the purity of the relugolix, it may be necessary or desirable to remove any or all unwanted salts from the relugolix by water extractions or to remove any or all other impurities before preparing the solution of relugolix in DCM.

Form B of anhydrous relugolix is also prepared by
   a) mixing a solution of relugolix in DCM wherein the relugolix is in at least about 20 volumes of DCM (weight($g_{relugolix}$):volume($mL_{DCM}$) with an anti-solvent wherein the anti-solvent is at about a 1:1 ratio of anti-solvent to DCM (volume$_{anti-solvent}$:volume$_{DCM}$);
   b) stirring the mixture of step a) for a period of time to yield Form B of anhydrous relugolix as a precipitate.

One embodiment further comprises preparing the solution of relugolix in DCM by dissolving relugolix in DCM. Another embodiment further comprises preparing the solution of relugolix in DCM by combining relugolix and DCM, wherein the relugolix is formed by a chemical reaction in solution, for example, by deprotection. In one embodiment, the stirring occurs overnight (about 16-24 h). One embodiment further comprises concentrating the solution of relugolix in DCM to a certain volume before mixing with the anti-solvent. In various embodiments, the anti-solvent is cumene, cyclohexane, TBME, heptane, or toluene. It will be apparent to one of ordinary skill in the art that any relugolix may be used, regardless of its solid-state form, in the solution of relugolix in DCM. Depending on the purity of the relugolix, it may be necessary or desirable to remove any or all unwanted salts from the relugolix by water extractions or to remove any or all other impurities before preparing the solution of relugolix in DCM. Another embodiment further comprises isolating the precipitate.

In one embodiment of the invention, Form T of anhydrous relugolix is prepared by:
   a) forming a solution of Form A of the DMF solvate of relugolix in an alcohol at an elevated temperature; and
   b) cooling the solution to yield Form T of anhydrous relugolix as a precipitate.

In one embodiment, the alcohol is methanol, ethanol, or isopropanol. In a particular embodiment, the alcohol is methanol. In one embodiment, the elevated temperature is about 50-60° C. In one embodiment, the alcohol is heated to the elevated temperature to form the solution. In another embodiment, a mixture of Form A of the DMF solvate of relugolix and alcohol is heated to the elevated temperature to form the solution. In one embodiment, about 7-10 volumes of alcohol (mL) is used per weight (g) of Form A of the DMF solvate of relugolix. In one embodiment, the cooling is to about 17-24° C. In one embodiment, the solution is stirred while cooling. In one embodiment, the precipitate is filtered. In a particular embodiment, the filtration is under vacuum. In one embodiment, the precipitate is washed one or more times with an alcohol. In one embodiment, the alcohol is methanol, ethanol, or isopropanol. In a particular embodiment, about 2-4 volumes (mL) of alcohol, particularly about 3 volumes, are used for the wash per weight (g) of Form A of the DMF solvate of relugolix. In one embodiment, the precipitate is dried. In a particular embodiment, the drying is in a vacuum oven. In a particular embodiment, the drying is at about 38° C. In one embodiment, the drying occurs for about 2-4 hours, particularly for about 3 hours.

In another embodiment of the invention, Form T of anhydrous relugolix is prepared by:
   a) mixing amorphous relugolix or Form B of anhydrous relugolix with an alcohol to form a slurry;
   b) stirring the slurry to yield Form T of anhydrous relugolix.

In one embodiment, the alcohol is methanol, ethanol, or a mixture of isopropanol/water. In a particular embodiment, the ratio of isopropanol:water is about 19:1 (v/v). In one embodiment, about 10-15 volumes of alcohol or alcohol/water mixture (mL) are used per weight (g) of amorphous relugolix or Form B of anhydrous relugolix. In one embodiment, the stirring is for about 24-48 hours. In one embodiment, the slurry of step b) is filtered. In one embodiment, Form T of anhydrous relugolix is washed with an alcohol. In one embodiment, the alcohol is methanol, ethanol, or a mixture of isopropanol/water. In a particular embodiment, about 2-4 volumes (mL) of alcohol, particularly about 3 volumes, are used for the wash per weight (g) of amorphous relugolix or Form B of anhydrous relugolix. In one embodiment, Form T of anhydrous relugolix is dried. In another embodiment, relugolix Form G or amorphous relugolix disclosed in WO2019/178304 can be mixed with an alcohol to form a slurry, wherein the alcohol is methanol, ethanol, or a mixture of isopropanol/water, and stirred to yield Form T of anhydrous relugolix.

EXAMPLES

Examples 1-6, which follow herein, disclose the preparation of Form A of the DMF solvate of relugolix, Form B of anhydrous relugolix, and Form T of anhydrous relugolix.

The Examples are presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are illustrative of the present disclosure and the disclosure is not intended to be limited to the examples described herein and shown.

Example 1

Preparation of Form a of the DMF Solvate of Relugolix 1.63 g of Form B of anhydrous relugolix is dissolved with DMF (7.6 g, 8.2 mL). The total solution weight (solvent+API) is 9.2 g. From that solution, equal amounts are transferred into two 100 mL RB (round bottom) Flasks equipped with the same size/shape magnetic stirring bar at the same agitation speed (about 700 RPMs); about 4.37 g of DMF/API solution (about 775 mg of API) is contained in each flask.

10.2 mL of TBME (about 13 volumes TBME (mL) to weight of API (g)) is added to one flask and 10.2 mL of toluene (about 13 volumes toluene (mL) to weight of API (g)) is added to the second flask. The contents of each flask are stirred. Signs of precipitation are shown within the first 10 minutes of agitation in the TBME flask. Signs of precipitation are shown the following day in the toluene flask.

The contents of each flask are separately vacuum filtered using a Buckner funnel with paper filter. Additional TBME (2×4 mL) is used to transfer all the material in the TBME flask onto the filter. The isolated material is dried under vacuum at about 45° C. for about 8 hours. 770 mg (89.5% isolated yield) of Form A of the DMF solvate of relugolix is obtained as a yellow solid and having a 1:1 API to DMF solvent ratio.

No additional toluene is required to transfer the material from the toluene flask onto the filter. The isolated material is dried under vacuum at about 45° C. for about 8 hours. 694 mg (80.3% isolated yield) of Form A of the DMF solvate of relugolix is obtained as a yellow solid and having a 1:1 API to DMF solvent ratio.

Form A of the DMF solvate of relugolix is stable, i.e., it is unchanged after prolonged drying (e.g., about 2 days) under vacuum at about 70° C. It also remains unchanged under about 97% humidity at ambient temperatures for over a month.

XRPD 2θ pattern peaks and relative % intensity values for the peaks of Form A of the DMF solvate of relugolix are shown in Table I.

TABLE 1

Average Peak List for Form A of the DMF solvate of relugolix

| Angle (2θ°) degree | Intensity % |
|---|---|
| 8.6 | 16.7 |
| 9.0 | 40.4 |
| 11.0 | 14.1 |
| 12.8 | 30.2 |
| 13.2 | 16.5 |
| 13.5 | 13.3 |
| 13.8 | 13.3 |
| 14.4 | 12.7 |
| 18.2 | 29.4 |
| 19.1 | 32.5 |
| 20.1 | 100 |
| 21.7 | 29 |
| 24.3 | 57.5 |
| 25.4 | 25.1 |
| 25.9 | 39.6 |
| 30.9 | 24.3 |

The angle measurements are ±0.2° 2θ. Key defining peaks for solid-state Form A of the DMF solvate of relugolix include two or more of 20.1, 24.3, and 9.0° 2θ.

Single crystal parameters for Form A of the DMF solvate of relugolix as determined by SCXRD are:
Crystal System: Triclinic Space Group P1
a=1.1 Å±1.5%
b=12.0 Å±1.5%
c=14.0 Å±1.5%
α=112°±3°
β=110°±3°
γ=91°±3°
Cell Volume: 1609 Å$^3$±3%

An XPRD pattern for a representative sample of Form A of the DMF solvate of relugolix (top) and a calculated XRPD pattern from a single crystal of Form A of the DMF solvate of relugolix (bottom) are shown in FIG. 1.

Figure 2:
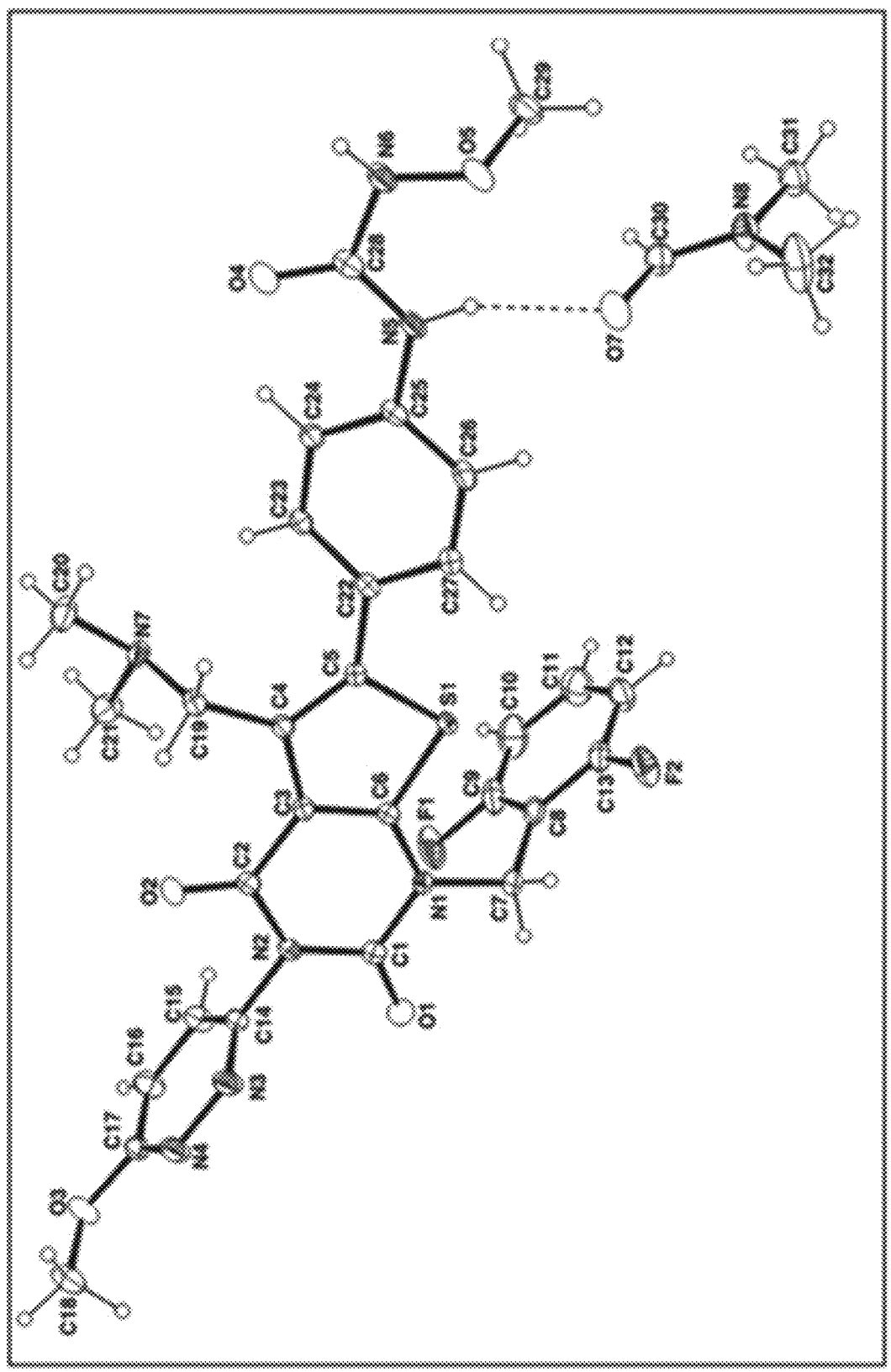
FIG. 2 provides a three-dimensional structure of Form A of the DMF solvate of relugolix that is discerned from SCXRD.

A three-dimensional structure of Form A of the DMF solvate of relugolix that is discerned from SCXRD is shown in FIG. 2.

Figure 3:
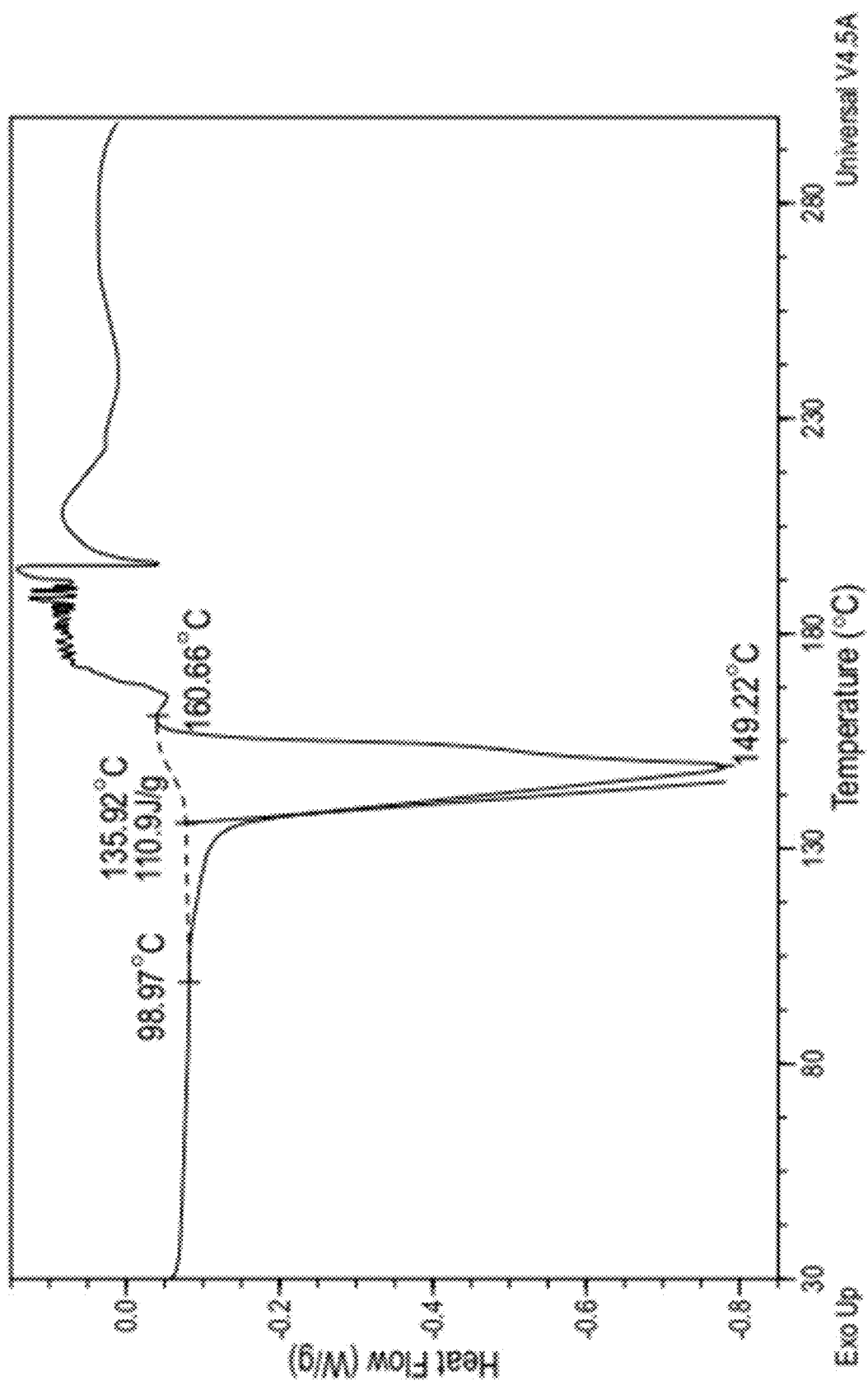
FIG. 3 provides a representative DSC plot of Form A of the DMF solvate of relugolix.
Figure 4:
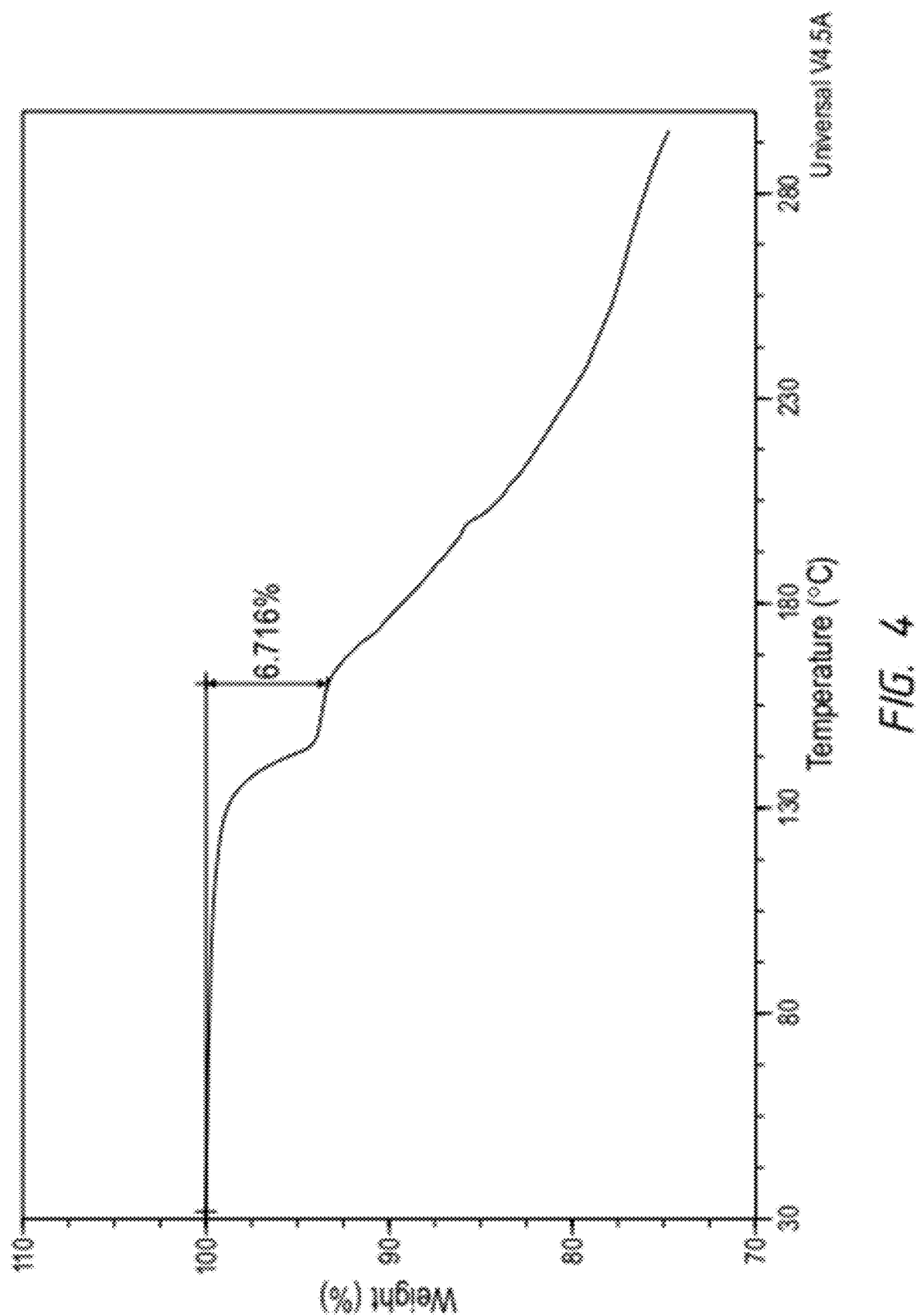
FIG. 4 provides a representative TGA plot of Form A of the DMF solvate of relugolix.

DSC analysis of Form A of the DMF solvate of relugolix shows the onset of an endothermic event at about 99° C. and a sharp endothermic event at about 149° C., as depicted in FIG. 3, and TGA analysis shows a loss of about 6.7 weight % up to about 155° C., as depicted in FIG. 4.

Figure 5:
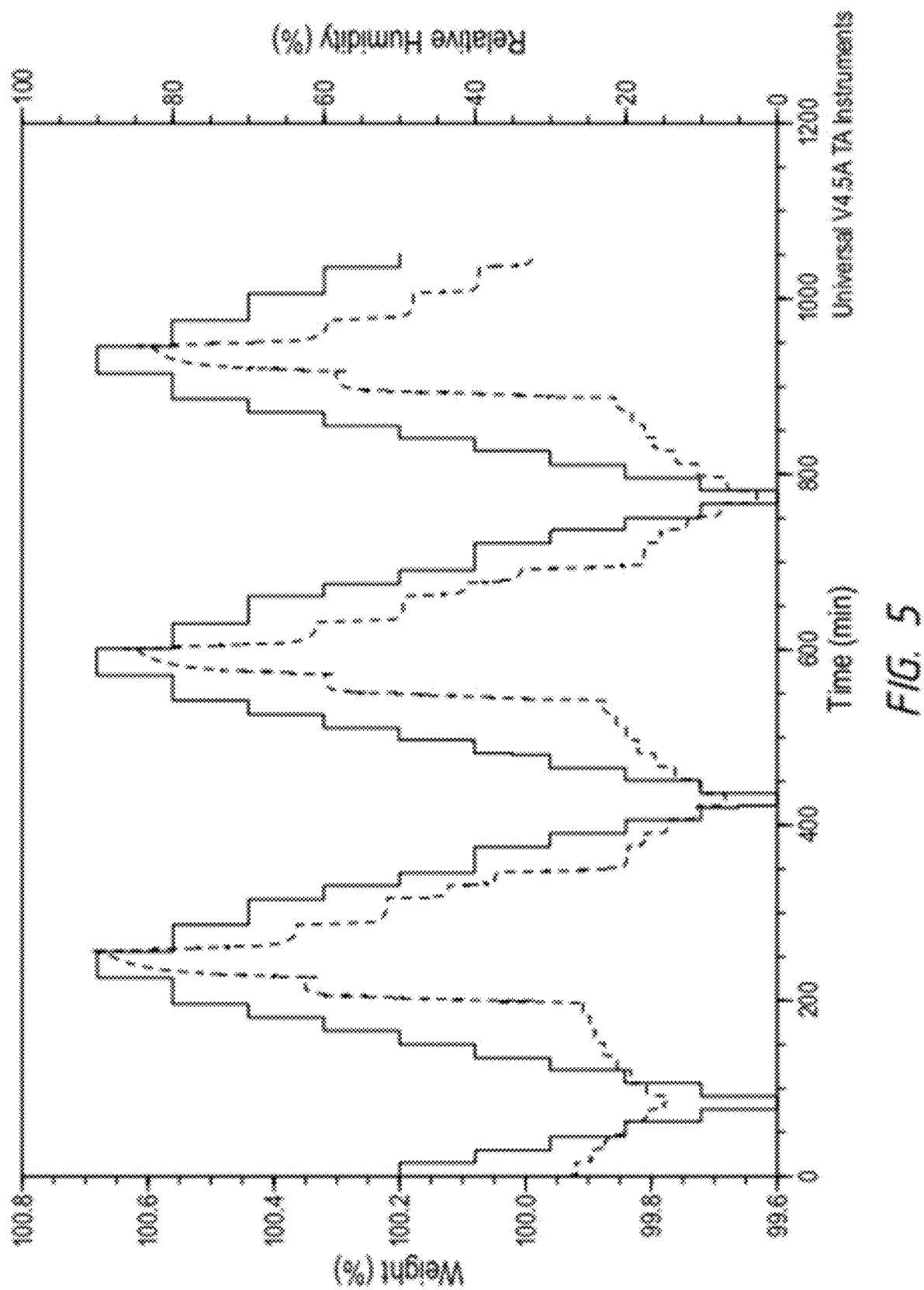
FIG. 5 provides a representative DVS plot of Form A of the DMF solvate of relugolix.

A representative DVS plot of Form A of the DMF solvate of relugolix indicates the loss of about 1% mass at about 90% RH, as depicted in FIG. 5.

Figure 6:
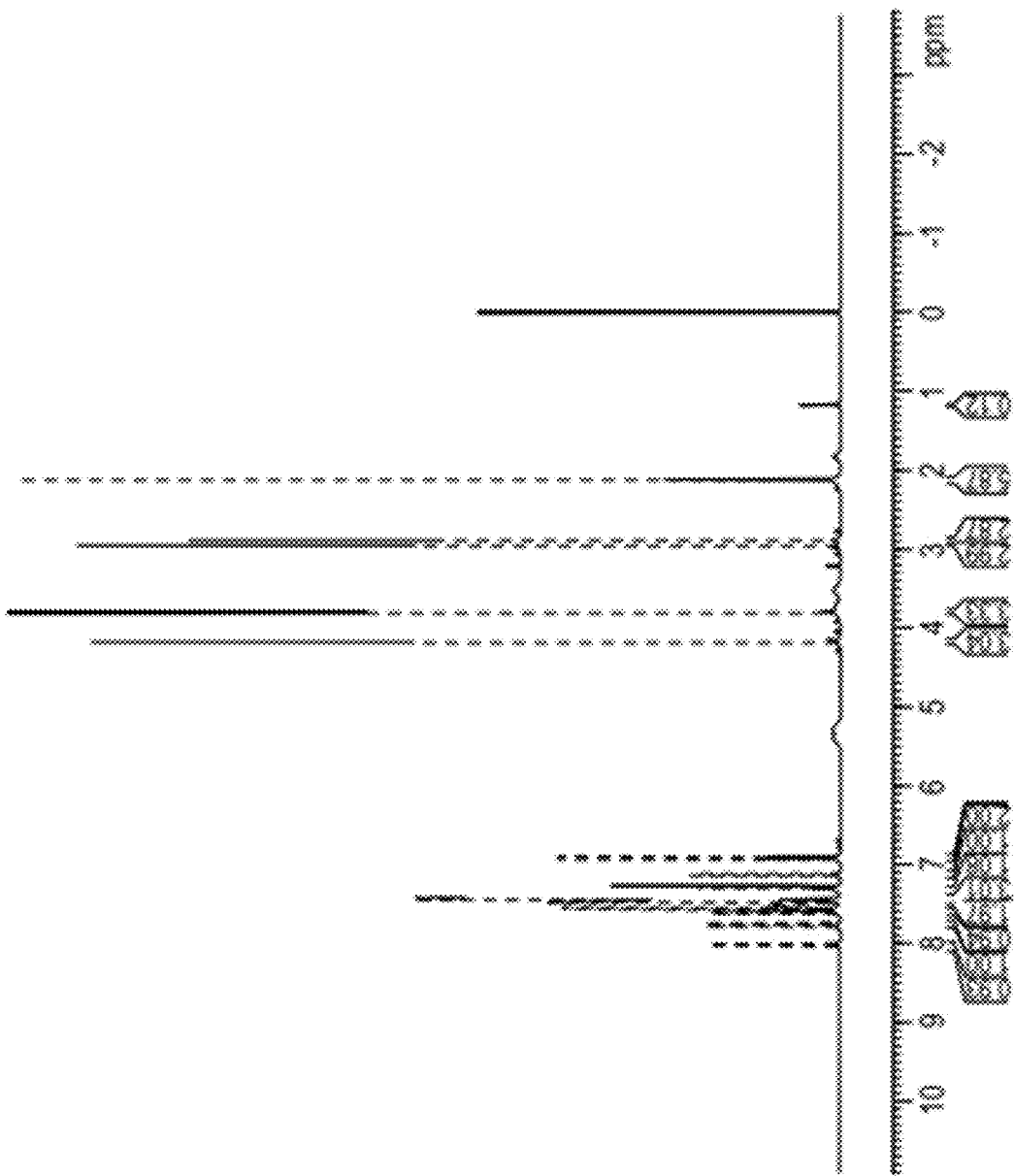
FIG. 6 provides a representative $^1$H-NMR plot of Form A of the DMF solvate of relugolix.

$^1$H NMR analysis indicates the presence of DMF in Form A of the DMF solvate of relugolix, as depicted in FIG. 6.

Example 2

Figure 7:
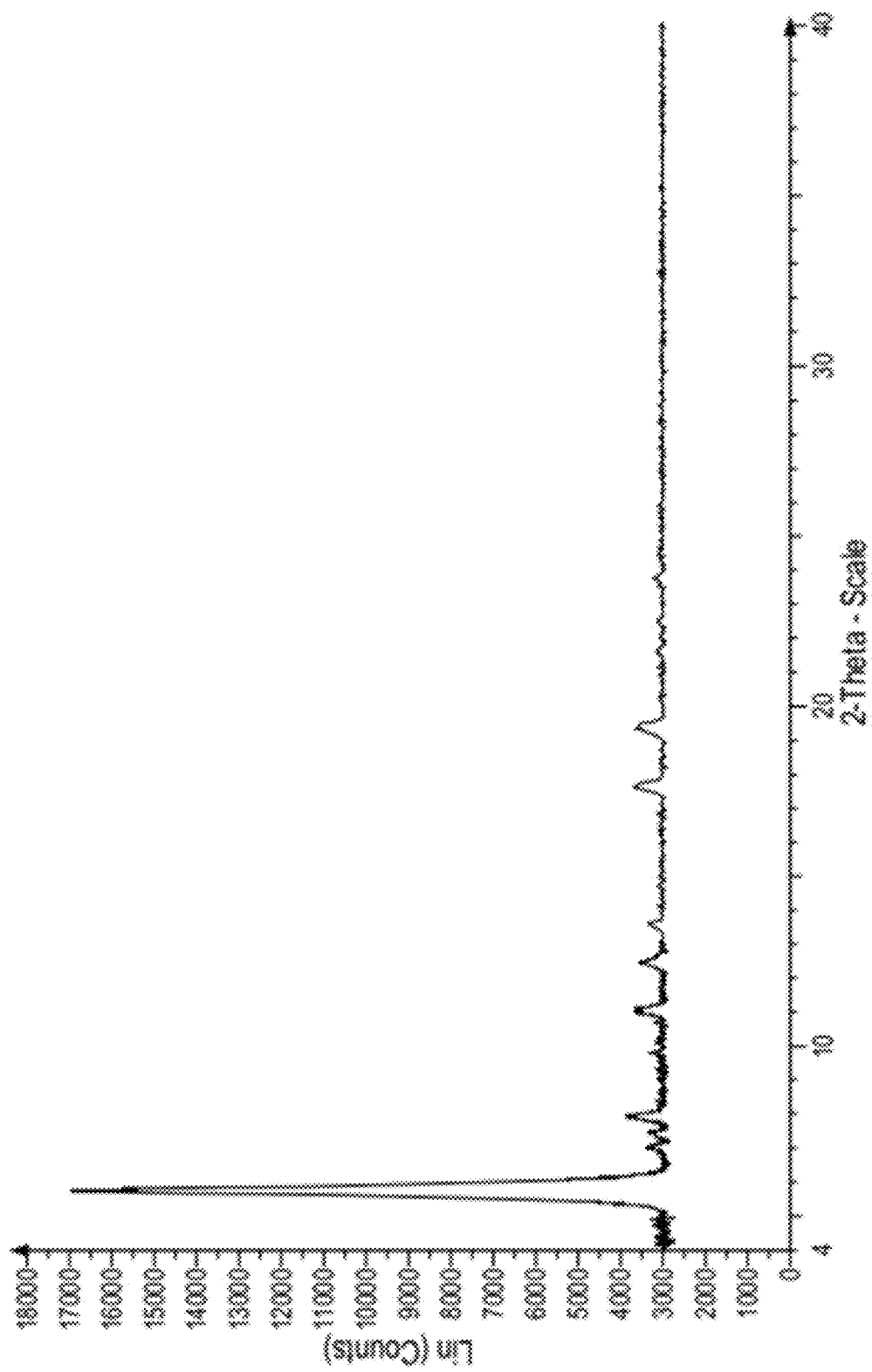
FIG. 7 provides a representative XRPD pattern of Form B of anhydrous relugolix.

Preparation of Form B of Anhydrous Relugolix 120 mL of DCM is added to 8.2 g of relugolix. The mixture is stirred for about 5 minutes, resulting in a slurry. About 100 mL of water is added to the slurry and stirred for about 15 minutes. After the stirring is stopped, some solids remain at the bottom of the flask and a bilayer is visible with a yellow organic bottom layer and mostly clear to hazy-clear aqueous layer on the top. The liquid is then decanted into a separatory funnel. 100 mL of DCM is added to the undissolved solids and stirred, forming a slurry. 100 mL of water is added to the slurry, stirred for about 15 minutes, and the liquid is decanted into the separatory funnel. 25 mL of DCM is added to any undissolved solids. The organic layer is vacuum filtered to remove any remaining solids. No drying agent is used to remove visible water droplets. The solvent in the organic layer is evaporated using a rotary evaporator at 35° C. and under a high vacuum pump for at least 3 hours. The isolated yellow solids (8.0 g, 97.6% yield) are identified as Form B of anhydrous relugolix. A representative XRPD pattern for Form B of anhydrous relugolix is shown in FIG. 7.

XRPD 2θ pattern peaks and relative % intensity values for the peaks of Form B of anhydrous relugolix are shown in Table 2.

TABLE 2

Average Peak List for Form B of anhydrous relugolix

| Angle (2θ°) degree | Intensity % |
|---|---|
| 5.7 | 100 |
| 7.0 | 20 |
| 7.4 | 19.6 |
| 7.9 | 22.5 |
| 9.8 | 19.3 |
| 11.0 | 21.7 |
| 12.4 | 21.1 |
| 13.5 | 19.6 |
| 17.6 | 21.6 |
| 19.4 | 21.3 |
| 21.6 | 18.5 |
| 23.7 | 19.1 |

The angle measurements are ±0.2° 2θ. A key defining peak for solid-state Form B of anhydrous relugolix includes 5.7° 2θ.

Figure 8:
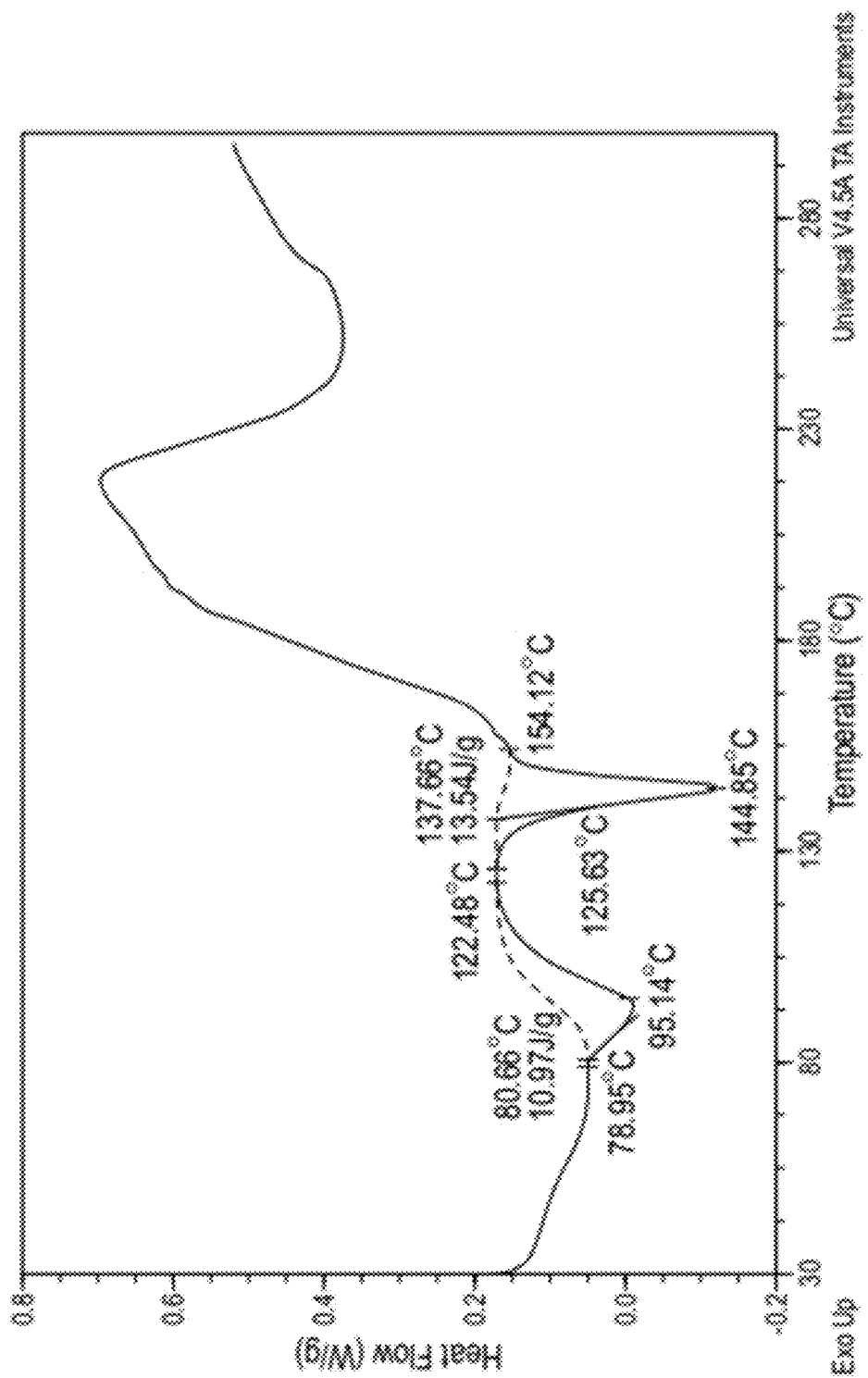
FIG. 8 provides a representative DSC plot of Form B of anhydrous relugolix.

DSC analysis of Form B of anhydrous relugolix shows a loss of solvent at an onset temperature of about 79° C. and the onset of an endothermic event at about 126° C. with an endothermic event at about 145° C., as depicted in FIG. 8.

Figure 9:
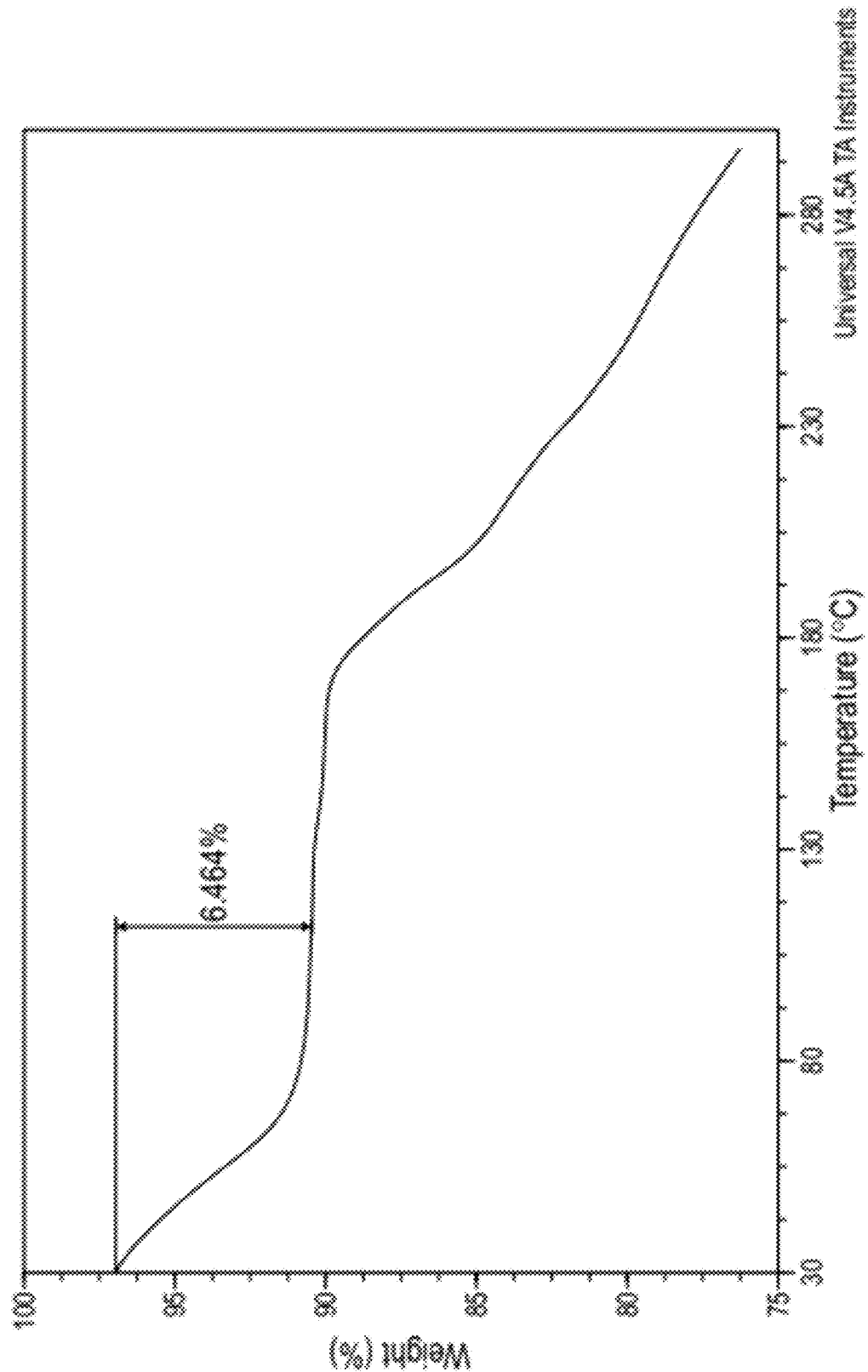
FIG. 9 provides a representative TGA plot of Form B of anhydrous relugolix.

TGA analysis shows a loss of greater than about 6 weight % up to about 105° C., as depicted in FIG. 9.

Figure 10:
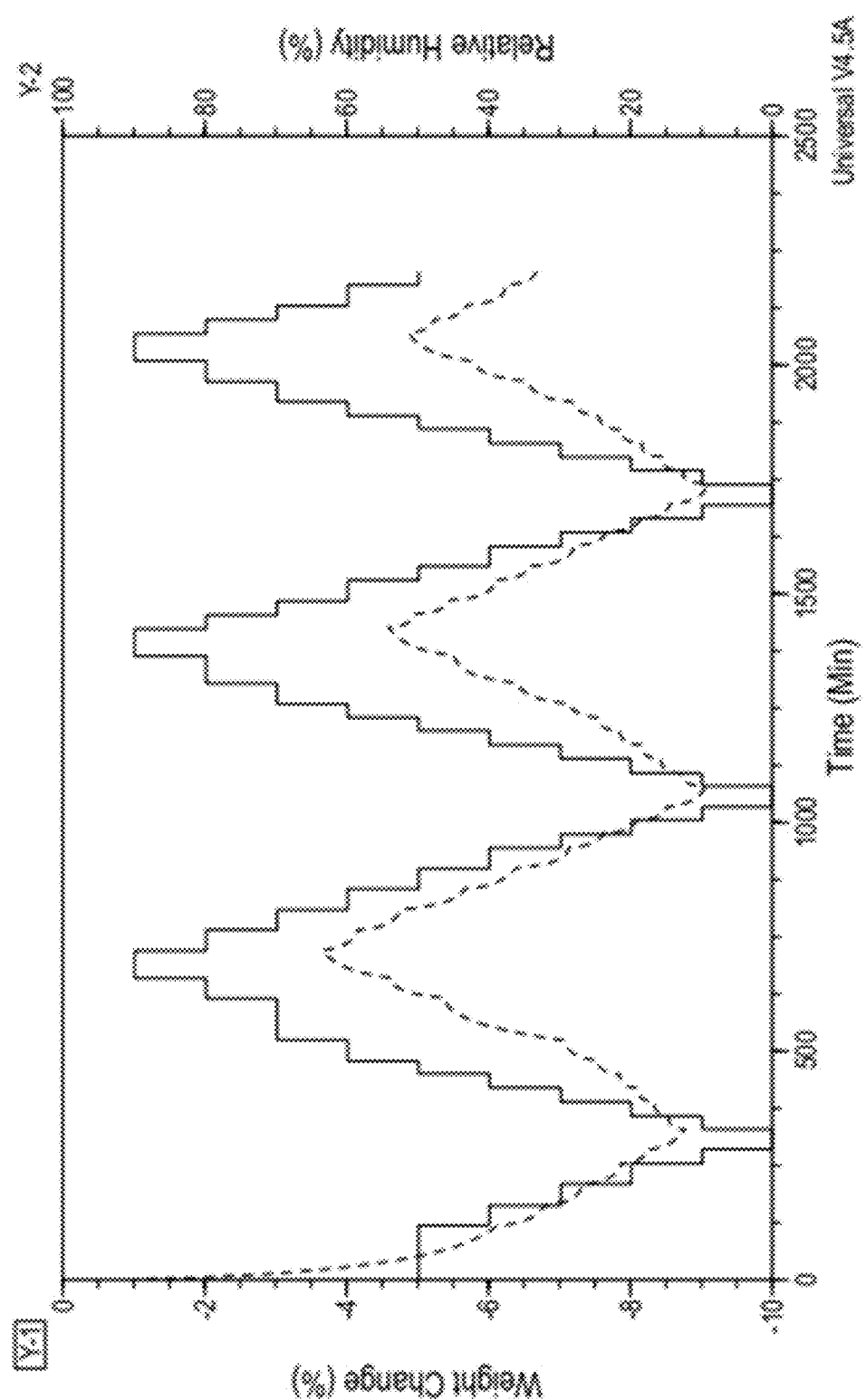
FIG. 10 provides a representative DVS plot of Form B of anhydrous relugolix.

DVS analysis of Form B of anhydrous relugolix shows a weight loss of about 7% at relative humidity levels between about 0 to about 95%, as depicted in FIG. 10.

Figure 11:
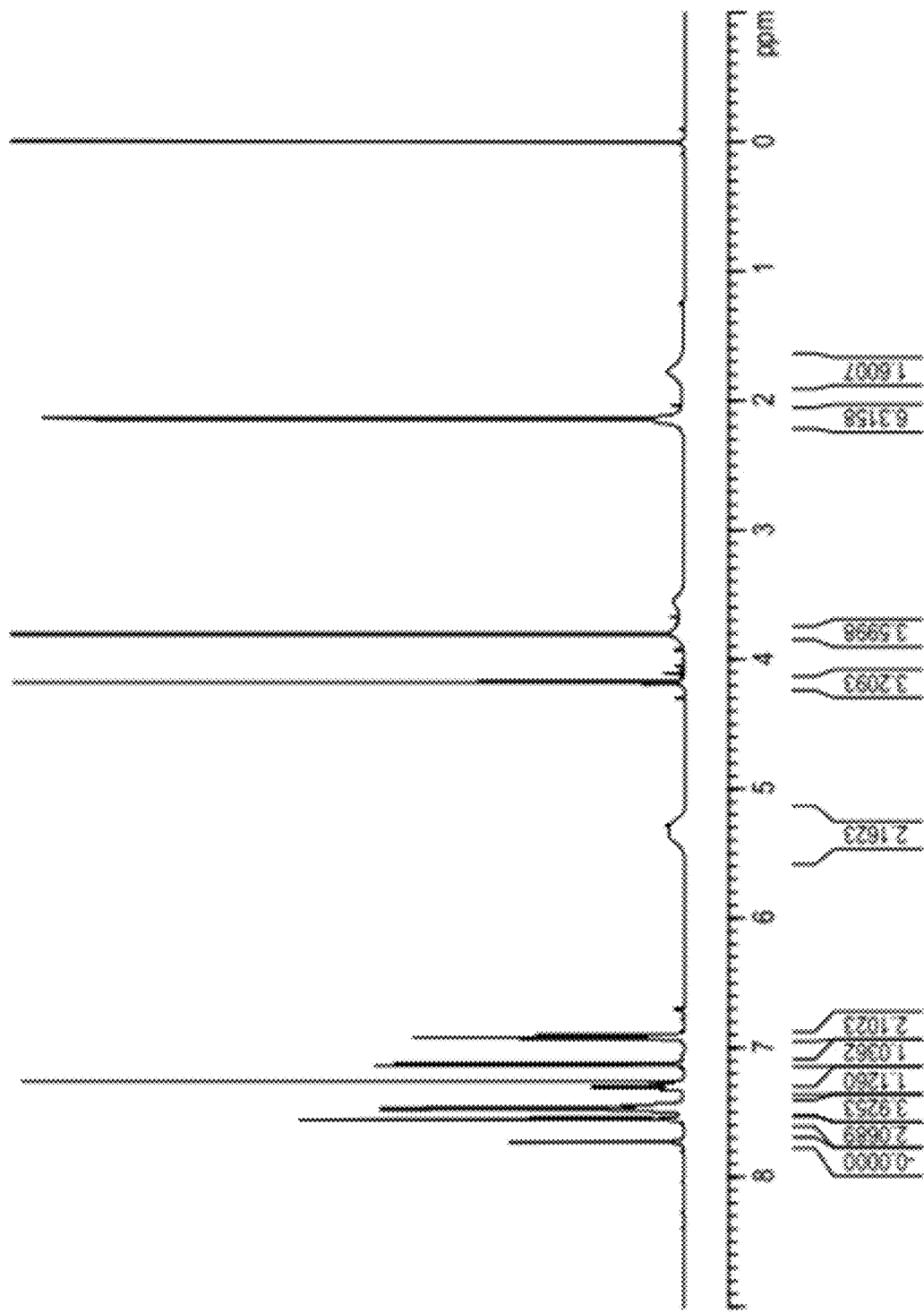
FIG. 11 provides a representative $^1$H-NMR plot of Form B of anhydrous relugolix.

¹H NMR analysis of Form B of anhydrous relugolix confirms its structure and is depicted in FIG. 11.

Form B of anhydrous relugolix remains stable at various humidity levels, as evidenced by XRPD after DVS.

Example 3

Preparation of Form T of Anhydrous Relugolix

Form A of the DMF solvate of relugolix (345 mg) are dissolved in 7 volumes of methanol (2.5 mL) at 60° C. The solution becomes clear within 5 minutes. The solution is allowed to cool to ambient temperature (17° C.) while stirring for one hour, resulting in a precipitate. The precipitate is vacuum filtered followed by a methanol wash (1 mL, 3 volumes). The solids are dried in a vacuum oven for 3 hours (30° C., −29.5 mmHg). A total of 230 mg of yellow solids are isolated and confirmed by XRPD to be Form T of anhydrous relugolix.

XRPD 2θ pattern peaks and relative % intensity values for the peaks of a representative sample of Form T of anhydrous relugolix are shown in Table 3.

TABLE 3

Average Peak List for Form T of anhydrous relugolix

| Angle (2θ°) degree | Intensity % |
|---|---|
| 7.5 | 55.4 |
| 9.1 | 49.7 |
| 10.1 | 41.4 |
| 10.4 | 15.4 |
| 11.5 | 35.4 |
| 12.2 | 55.2 |
| 12.5 | 16.1 |
| 13.3 | 17.2 |
| 13.5 | 14.7 |
| 15.0 | 49 |
| 16.6 | 52.2 |
| 16.8 | 100 |
| 17.5 | 76.2 |
| 18.1 | 15 |
| 18.8 | 19.3 |
| 19.0 | 16.9 |
| 19.5 | 37.9 |
| 20.1 | 19.6 |
| 20.3 | 15 |
| 21.4 | 17 |
| 21.9 | 25.6 |
| 22.1 | 28.1 |
| 22.4 | 58 |
| 22.9 | 56.5 |
| 23.1 | 21.5 |
| 23.7 | 19.5 |
| 24.6 | 19 |
| 26.7 | 23 |
| 27.6 | 28.1 |
| 29.1 | 23.3 |
| 29.8 | 24.7 |

The angle measurements are ±0.2° 2θ. Key defining peaks for solid-state Form T of anhydrous relugolix include peaks at about 16.8 and 17.5°±0.2° 2θ. Other peaks for solid-state Form T of anhydrous relugolix include 7.5, 9.1, 10.1, 12.2, 22.4, and 22.9° 0.2° 2θ.

Single crystal parameters for Form T of anhydrous relugolix as determined by SCXRD are:

Crystal System: Monoclinic
Space Group: P 2₁/n
a=10.5 Å±1.5%
b=17.5 Å±1.5%
c=16.3 Å±1.5%
α=γ=90°, β=105°±3°
Cell Volume: 2616 Å³±3%

Figure 12:
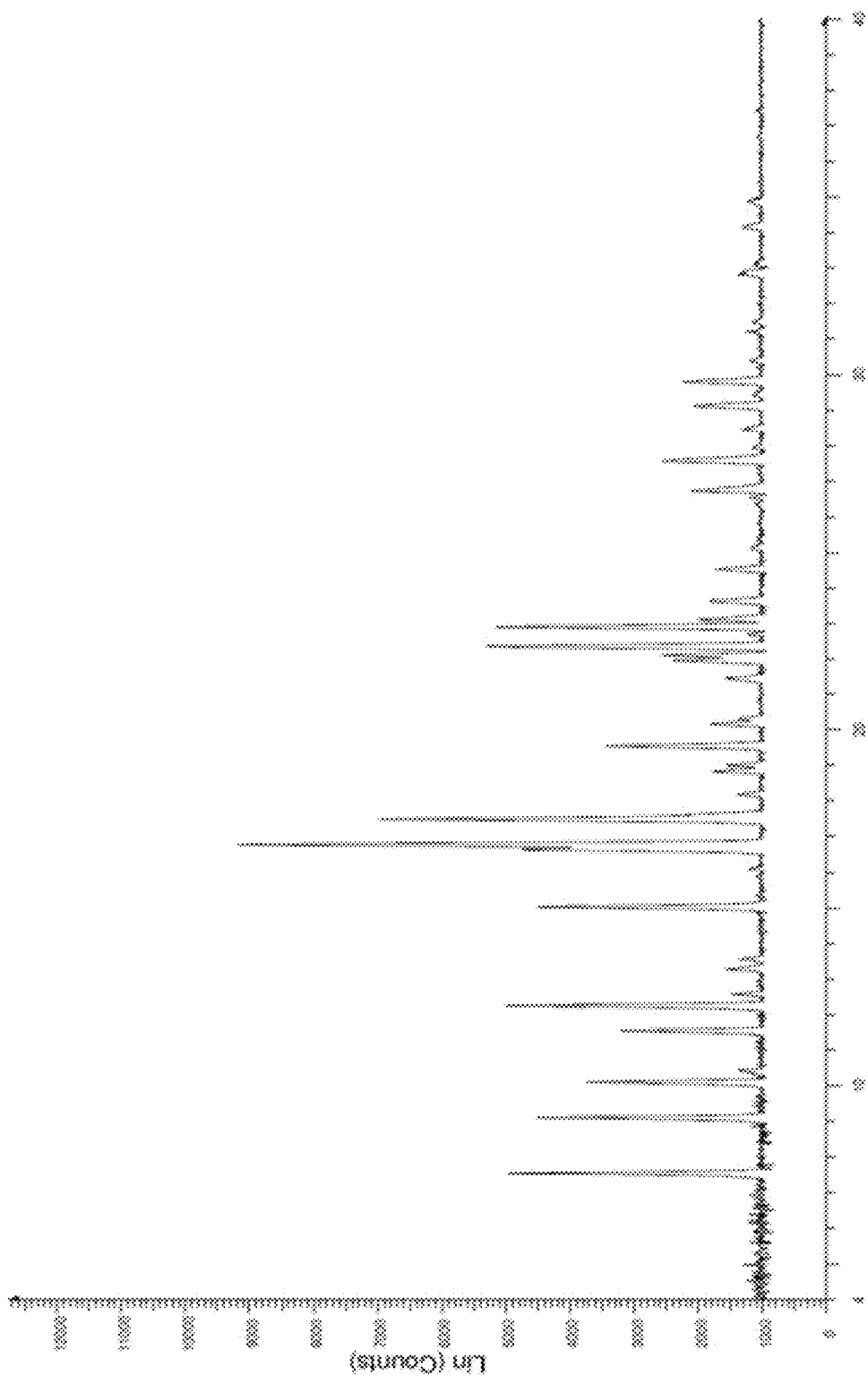
FIG. 12 provides a representative XRPD pattern of Form T of anhydrous relugolix.

An XPRD pattern for a representative sample of Form T of anhydrous relugolix is shown in FIG. 12.

Figure 13:
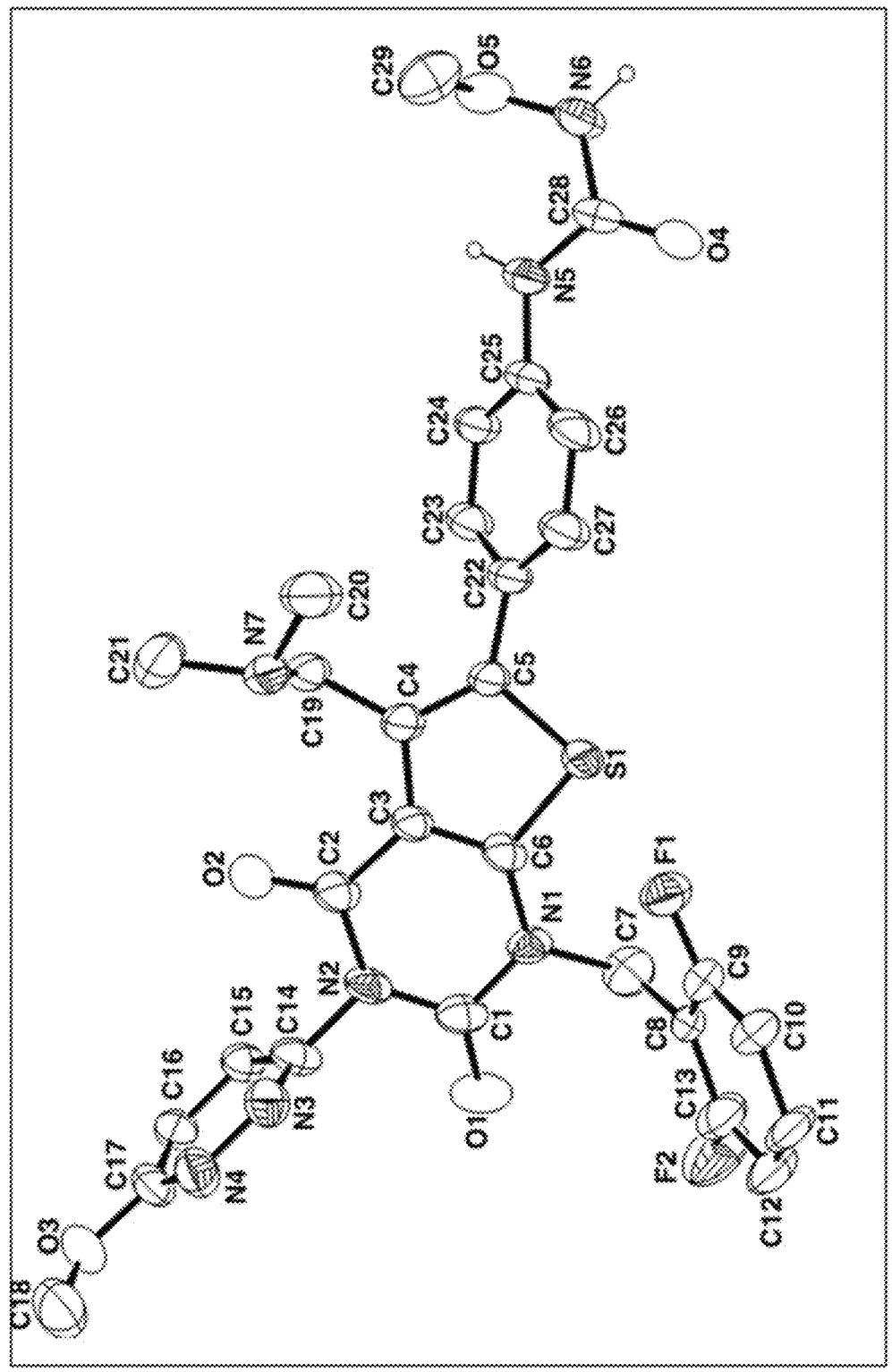
FIG. 13 provides a three-dimensional structure of Form T of anhydrous relugolix that is discerned from SCXRD.

A three-dimensional structure of Form T of anhydrous relugolix that is discerned from SCXRD is shown in FIG. 13.

Figure 14:
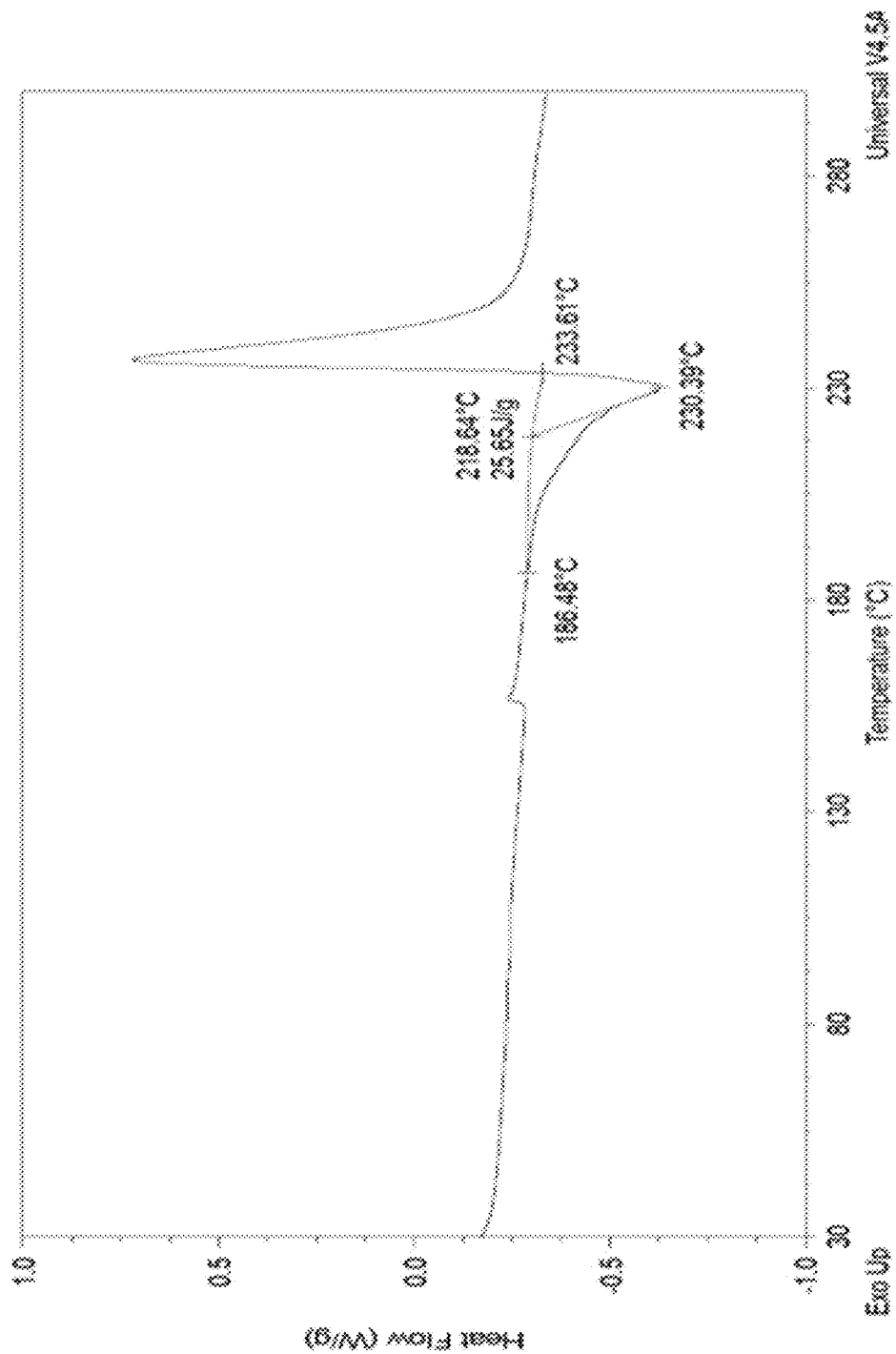
FIG. 14 provides a representative DSC plot of Form T of anhydrous relugolix.
Figure 15:
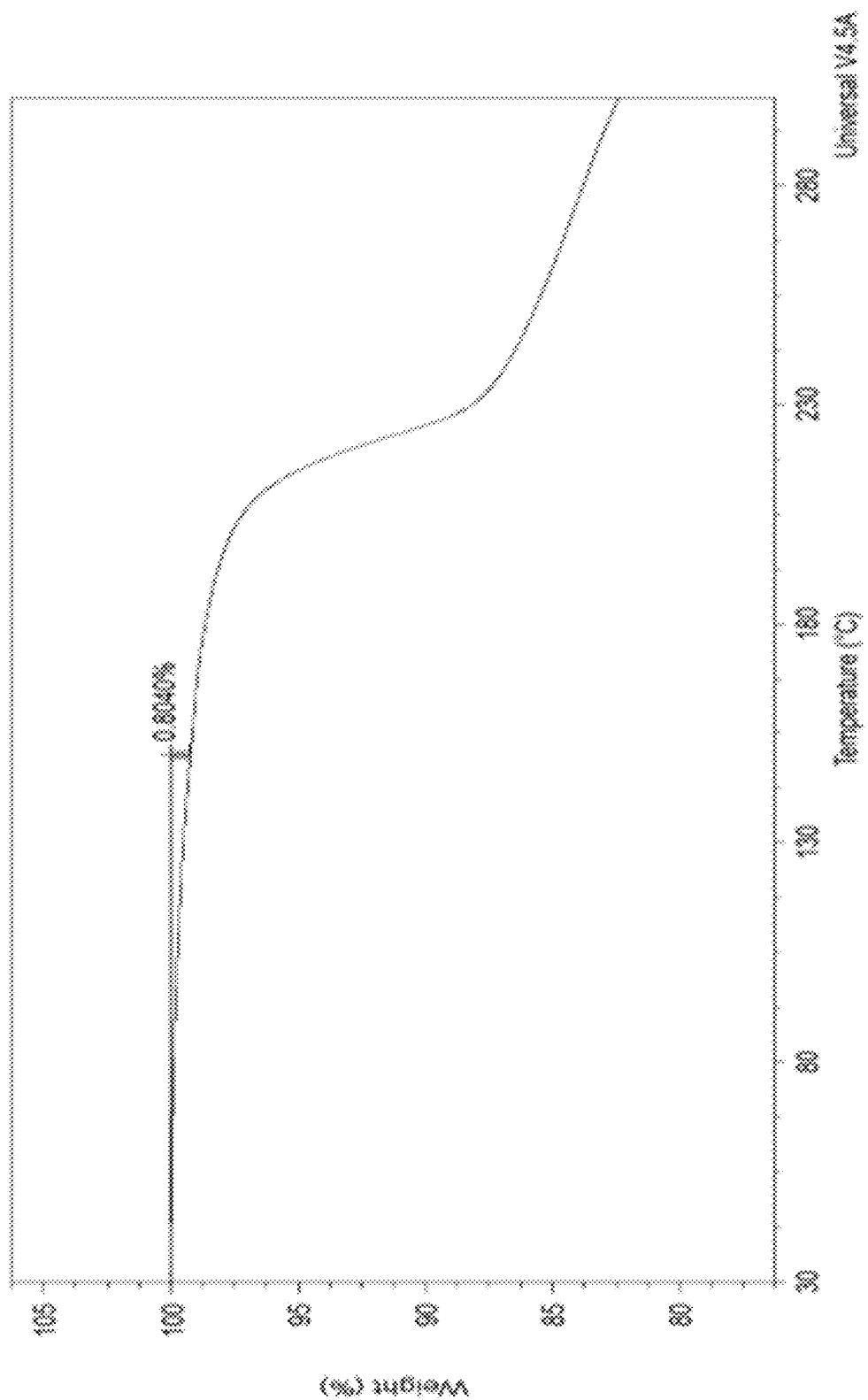
FIG. 15 provides a representative TGA plot of Form T of anhydrous relugolix.

A representative DSC analysis of Form T of anhydrous relugolix shows the onset of an endothermic event at about 186.5° C., as depicted in FIG. 14, and a representative TGA analysis shows a loss of about 0.8 weight % up to about 145° C., as depicted in FIG. 15.

Figure 16:
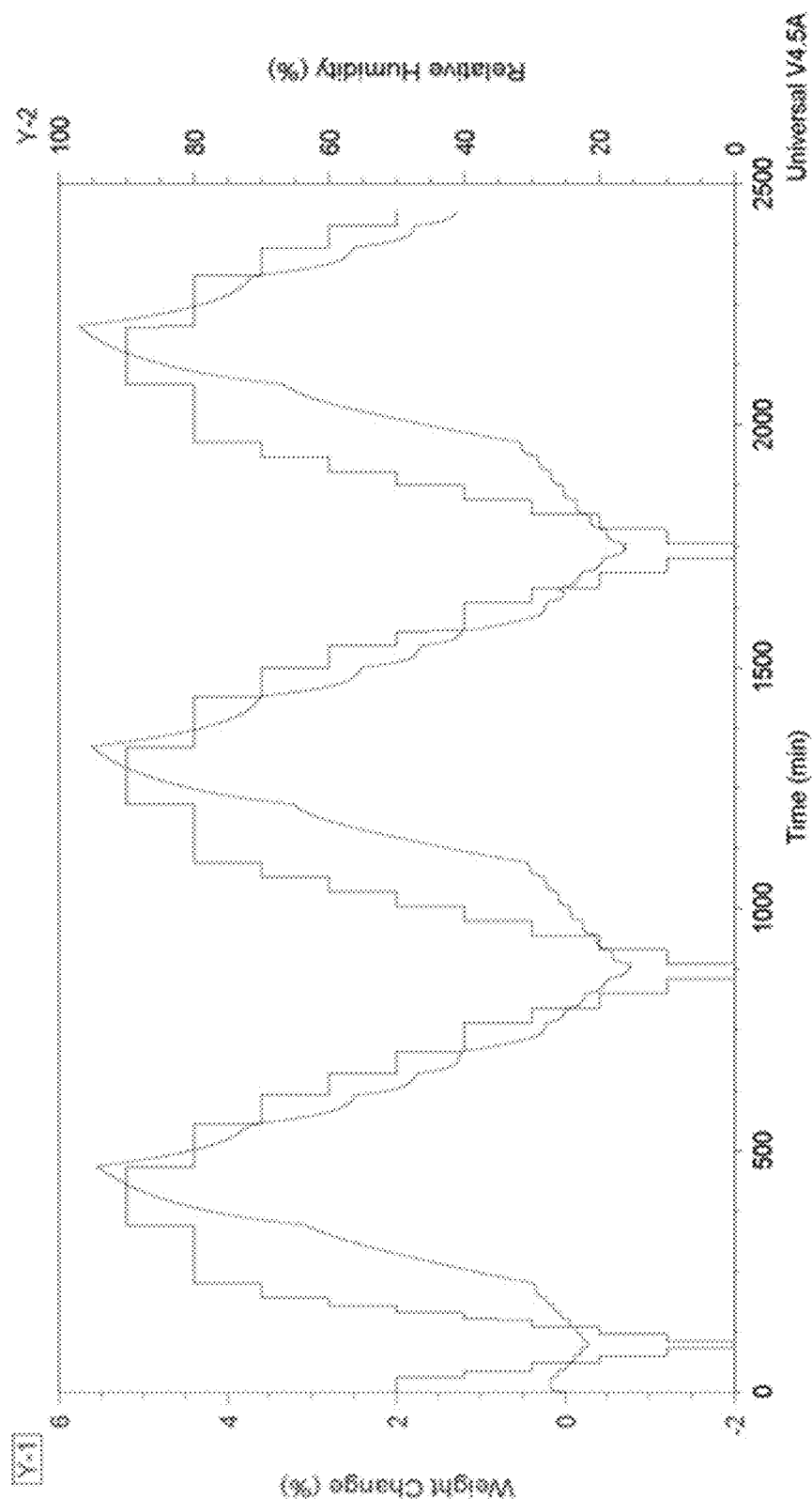
FIG. 16 provides a representative DVS plot of Form T of anhydrous relugolix.

A representative DVS plot of Form T of anhydrous relugolix indicates a weight % change of about 6% when exposed to relative humidity (RH) levels between 0 to 90%, as depicted in FIG. 16.

Figure 17:
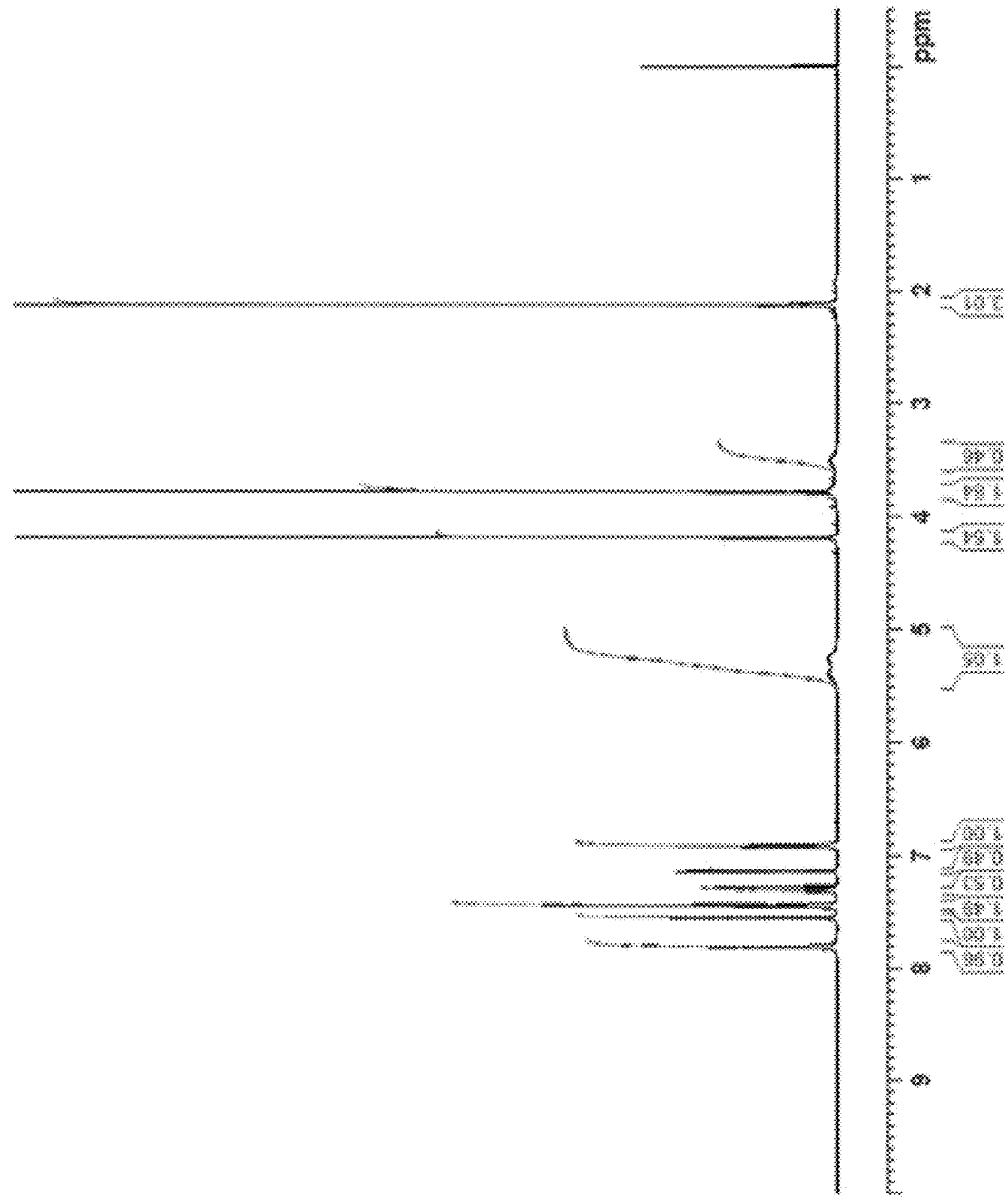
FIG. 17 provides a representative $^1$H-NMR plot of Form T of anhydrous relugolix.

¹H NMR analysis of a representative sample of Form T of anhydrous relugolix is depicted in FIG. 17.

Example 4

Preparation of Form T of Anhydrous Relugolix 5 g of relugolix anhydrous solids are mixed in DCM (250 mL, 50 volumes) and water (2×75 mL). After the extractions, the cloudy organic portion is mixed in MgSO₄ and filtered to a clear yellow solution. The solution is concentrated under vacuum with a rotary evaporator. The isolated solids are dissolved in DMF (15 mL, 5 volumes) to a thick yellow solution. TBME (used in access, 80-100 mL) is added to the DMF/API mixture in large portions. Clouding occurs followed by some oiling which over some time becomes mixable solids. The solids are filtered under vacuum with filter paper and checked by XRPD and confirmed to be Form A of the DMF solvate of relugolix.

The isolated Form A of the DMF solvate of relugolix which is still wet with mostly TBME is placed in a RBF (250 mL capacity) containing methanol (45 mL, 9 volumes). The slurry is heated to internal temperature of 51° C. and almost all of the slurry becomes a clear solution. Heating is stopped and the temperature is allowed to cool to ambient temperature (17° C.), resulting in a precipitate. The precipitate is vacuum filtered and dried in an oven at 38° C. for three hours resulting in 3.6 g, an overall isolated yield of about 72%. XRPD analysis confirms the precipitate is Form T of anhydrous relugolix.

Example 5

Preparation of Form T of Anhydrous Relugolix

About 95-102 mg of Form B of anhydrous relugolix is dispensed in a 2 mL-glass vial and about 1 mL of methanol is added to the vial at ambient temperature (20° C.) and stirred for 24 hours. The slurry is centrifuged at 20° C. The solids are tested by XRPD analysis which are confirmed to be Form T of anhydrous relugolix.

Example 6

Preparation of Form T of Anhydrous Relugolix

About 95-102 mg of Form B of anhydrous relugolix is dispensed in a 2 mL-glass vial and about 1.5 mL of ethanol is added to the vial at ambient temperature (20° C.) and stirred for 24 hours. The slurry is centrifuged at 20° C. The solids are tested by XRPD analysis which are confirmed to be Form T of anhydrous relugolix.

The above examples are set forth to aid in the understanding of the disclosure and are not intended and should not be construed to limit in any way the disclosure set forth in the claims which follow hereafter.

The invention claimed is:

1. A process for the preparation of Form T of anhydrous relugolix comprising:
   a) forming a solution of Form A of the DMF solvate of relugolix in an alcohol at an elevated temperature; and
   b) cooling the solution to yield Form T of anhydrous relugolix as a precipitate.

2. The process of claim 1 wherein the alcohol is methanol, ethanol, or isopropanol.

3. The process of claim 1, wherein the elevated temperature is about 50-60° C.

4. The process of claim 1, wherein the alcohol is heated to the elevated temperature to form the solution.

5. The process of claim 1, wherein a mixture of Form A of the DMF solvate of relugolix and alcohol is heated to the elevated temperature to form the solution.

6. The process of claim 1, wherein about 7-10 volumes of alcohol (mL) is used per weight (g) of Form A of the DMF solvate of relugolix.

7. The process of claim 1, wherein the cooling is to about 17-24° C.

8. The process of claim 1, wherein the solution is stirred while cooling.

9. The process of claim 1, wherein the precipitate is filtered.

10. The process of claim 1, wherein the precipitate is washed one or more times with an alcohol.

11. The process of claim 10, wherein about 2-4 volumes (mL) of alcohol are used per weight (g) of Form A of the DMF solvate of relugolix.

12. The process of claim 10, wherein the alcohol is methanol, ethanol, or isopropanol.

13. The process of claim 1, wherein the precipitate is dried.

14. A process for the preparation of Form T of anhydrous relugolix comprising:
   a) mixing amorphous relugolix or Form B of anhydrous relugolix with an alcohol to form a slurry; and
   b) stirring the slurry to yield Form T of anhydrous relugolix.

15. The process of claim 14, wherein the alcohol is methanol, ethanol, or an isopropanol/water mixture.

16. The process of claim 15, wherein the ratio of isopropanol:water is about 19:1 (v/v).

17. The process of claim 14, wherein about 10-15 volumes of alcohol (mL) is used per weight (g) of amorphous relugolix or Form B of anhydrous relugolix.

18. The process of claim 14, wherein the stirring is for about 24-48 hours.

19. The process of claim 14 further comprising filtering the slurry of step b.

20. The process of claim 14, wherein Form T of anhydrous relugolix is washed with an alcohol.

21. The process of claim 20, wherein the alcohol is selected from methanol, ethanol and an isopropanol/water mixture.

22. The process of claim 20, wherein about 2-4 volumes (mL) of alcohol are used for the wash per weight (g) of amorphous relugolix or Form B of anhydrous relugolix.

* * * * *